(12) United States Patent
Gannon et al.

(10) Patent No.: US 8,142,809 B2
(45) Date of Patent: Mar. 27, 2012

(54) COMPOSITIONS AND METHODS TO LOWER GLYCOHEMOGLOBIN LEVELS

(75) Inventors: Mary C. Gannon, Eagan, MN (US); Frank Nuttall, Eagan, MN (US)

(73) Assignees: Regent of the Univ. of Minnesota, Saint Paul, MN (US); The United States of America as represented by the Department of Veterans Affairs, Washington, DC (US)

( * ) Notice: Subject to any disclaimer, the term of this patent is extended or adjusted under 35 U.S.C. 154(b) by 717 days.

(21) Appl. No.: 11/660,682

(22) PCT Filed: Aug. 25, 2005

(86) PCT No.: PCT/US2005/030483
§ 371 (c)(1), (2), (4) Date: Feb. 21, 2007

(87) PCT Pub. No.: WO2006/026471
PCT Pub. Date: Mar. 9, 2006

(65) Prior Publication Data
US 2008/0031925 A1 Feb. 7, 2008

Related U.S. Application Data

(60) Provisional application No. 60/604,271, filed on Aug. 25, 2004.

(51) Int. Cl.
*A61K 47/00* (2006.01)
*A23B 7/148* (2006.01)
*A23D 9/013* (2006.01)
*A23L 1/30* (2006.01)

(52) U.S. Cl. ......... 424/439; 426/106; 426/531; 426/648

(58) Field of Classification Search .................. None
See application file for complete search history.

(56) References Cited

U.S. PATENT DOCUMENTS

| | | | |
|---|---|---|---|
| 4,670,268 | A | 6/1987 | Mahmoud |
| 5,904,948 | A | 5/1999 | Sartorio et al. |
| 6,017,550 | A | 1/2000 | Berk et al. |
| 6,171,640 | B1 | 1/2001 | Bringe |
| 6,762,035 | B1 * | 7/2004 | Gupta ............................. 435/26 |
| 2003/0154504 | A1 * | 8/2003 | Farese et al. .................... 800/18 |
| 2005/0058766 | A1 * | 3/2005 | Han .............................. 426/658 |

OTHER PUBLICATIONS

Cordain, L., and S.B. Eaton, J.B. Miller, N. Mann, and K. Hill. 2002. The Paradoxical Nature of Hunter-gatherer Diets: Meat-Based, yet Non-atherogenic. Eur. J. Clin. Nutr.; 56 Suppl. 1: S42-S52.*
Nuttall, F.Q., and M.C. Gannon, A. Saeed, K. Jordan, and H. Hoover. 2003. The Metabolic Response of Subjects with Type 2 Diabetes to a High-protein, Weight-maintenance Diet. J. Clin. Endocrinol. Metab.; 88(8): 3577-3583.*
Gannon, M.C., F.Q. Nuttall, S.A. Westphal, S. Fang, and N. Ercan-Fang. 1998. Acute Metabolic Response to High-Carbohydrate, High-Starch Meals Compared with Moderate-Carbohydrate, Low-Starch Meals in Subjects with Type-2 Diabetes. Diabetes Care 21(10): 1619-1626.*
Nuttall, F.Q., M.C. Gannon, A. Saeed, K. Jordan, and H. Hoover. 2003. The Metabolic Response of Subjects with Type-2 Diabetes to a High-Protein, Weight-Maintenance Diet. J. Clin. Endocrinol.Metab. 88(8): 3577-3583.*
Gannon, M.C., F.Q. Nuttall, S.A. Westphal, S. Fang, and N. Ercan-Fang. 1998. Acute Metabolic Response to High-Carbohydrate, High-Starch Meals Compared with Moderate-Carbohydrate, Low-Starch Meals in Subjects with Type-2 Diabetes. Diabetes Care; 21(10): 1619-1626.*
Nuttall, F.Q., M.C. Gannon, A. Saeed, K. Jordan, and H. Hoover. 2003. The Metabolic Response of Subjects with Type-2 Diabetes to a High-Protein, Weight-Maintenance Diet. J. Clin. Endocrinol. Metab.; 88(8): 3577-3583.*
Nuttall, F.Q., M.C. Gannon, A. Saeed, K. Jordan, and H. Hoover. 2003. The Metabolic Response of Subjects with Type 2 Diabetes to a High-Protein, Weight-Maintenance Diet. J. Clin. Endocrinol. Metab.; 88(8): 3577-3583.*
PCT International Search Report and Written Opinion ( 7 pp.).
Report of the Expert Committee on the Diagnosis and Classification of Diabetes Mellitus. Diabetes Care, vol. 21, Supplement 1, S5-S19, Jan. 1998.
Dietary Guidelines for Healthy American Adults, A Statement for Physicians and Health Professionals by Nutrition Committee, American Heart Association, Circulation vol. 74, No. 6, 1465A-1468A, Dec. 1986.
The Food Guide Pyramid, USDA. Washington DC, US Government Printing Office, 1992 (2 pages).
Nutrition and Your Health: Dietary Guidelines for Americans, U.S. Department of Agriculture and U.S. Department of Health and Human Services, Washington DC, US Government Printing Office, Fourth Edition, 1995 (1 page).
Watson, Patricia E., Watson, Ian D., Batt, Richard D., Total body water volumes for adult males and females estimated from simple anthropometric measurements. The American Journal of Clinical Nutrition 33:27-39, Jan. 1980.
Gannon, Mary C., Nuttall, Frank Q., Saeed, Asad, Jordan, Kelly and Hoover, Heidi. An increase in dietary protein improves the blood glucose response in persons with type 2 diabetes, Am J Clin Nutr 2003:78:734-41, 2003 American Society for Clinical Nutrition.
Nuttall, Frank Q., Schweim, Kelly, Hoover, Heidi and Gannon, Mary C. Effect of the LoBAG$_{30}$ diet on blood glucose control in people with type 2 diabetes. British Journal of Nutrition, 99, pp. 511-519, 2008.
Gannon, Mary C. and Nuttall, Frank Q. Effect of a High-Protein, Low-Carbohydrate Diet on Blood Glucose Control in People With Type 2 Diabetes. Diabetes, vol. 53:2375-2382, Sep. 2004.
Nuttall, Frank Q., Schweim, Kelly, Hoover Heidi and Gannon, Mary C. Metabolic effect of a LoBAG30 diet in men with type 2 diabetes. Am J Physiol Endocrinol Metab 291:E786-E791, 2006.

(Continued)

*Primary Examiner* — Carlos Azpuru
*Assistant Examiner* — David Browe
(74) *Attorney, Agent, or Firm* — Dinesh Agarwal, P.C.

(57) ABSTRACT

The invention provides for a diet that significantly reduces the glycohemoglobin levels in individuals with type 2 diabetes. A diet plan can be provided to an individual in the form of cards and/or pages with an appropriate meal plan, food items and/or pre-packaged meals, or in an electronic medium for the individuals to use to develop appropriate meal plans. The diet comprises food items having a nutritional composition that consists essentially of 30% protein, 50% fats, and 20% carbohydrates, or food items having a nutritional composition that consists essentially of 30% protein, 40% fats, and 30% carbohydrates.

4 Claims, 7 Drawing Sheets

OTHER PUBLICATIONS

Nuttall, Frank Q. and Gannon, Mary C. The metabolic response to a high-protein, low-carbohydrate diet in men with type 2 diabetes mellitus. Metabolism Clinical and Experimental 55 (2006) 243-251.
O'Dea, K. Marked Improvement in Carbohydrate and Lipid Metabolism in Diabetic Australian Aborigines After Temporary Reversion to Traditional Lifestyle. Diabetes. vol. 33:596-603, Jun. 1984.
O'Dea K, Traianedes K, Ireland P, Niall M, Sadler J, Hopper J and De Luise M. The effects of diet differing in fat, carbohydrate, and fiber on carbohydrate and lipid metabolism in Type II diabetes. Journal of the American Dietetic Association, vol. 89:1076-1086, Aug. 1989.
Wolfe BM and Giovannetti PM. Short-Term Effects of Substituting Protein for Carbohydrate in the Diets of Moderately Hypercholesterolemic Human Subjects. Metabolism, vol. 40, No. 4:338-343, Apr. 1991.
Wolfe BMJ and Piche LA. Replacement of carbohydrate by protein in a conventional-fat diet reduces cholesterol and triglyceride concentrations in healthy normolipidemic subjects. Clin Invest Med. vol. 22(4):140-8, 1999.
Wolfe BM and Giovannetti. High protein diet complements resin therapy of familial hypercholesterolemia. Clin. Invest Med., vol. 15:4 pp. 349-359, 1992.
Nuttall FQ, Khan MA, Gannon MC: Peripheral glucose appearance rate following fructose ingestion in normal subjects. Metabolism 2000;49:1565-1571.
Gannon MC, Khan MA, Nuttall FQ: Glucose appearance rate after the ingestion of galactose. Metabolism 2001;50:93-98.
Nuttall FQ, Mooradian AD, Gannon MC, Billington C, Krezowski P: Effect of protein ingestion on the glucose and insulin response to a standardized oral glucose load. Diabetes Care 1984;7:465-470.
Krezowski PA, Nuttall FQ, Gannon MC, Bartosh NH: The effect of protein ingestion on the metabolic response to oral glucose in normal individuals. Am J Clin Nutr 1986;44:847-856.
Gannon MC, Nuttall FQ, Neil BJ, Westphal SA: The insulin and glucose responses to meals of glucose plus various proteins in type II diabetic subjects. Metabolism 1988;37:1081-1088.
Khan MA, Gannon MC, Nuttall FQ: Glucose appearance rate following protein ingestion in normal subjects. J Am Coll Nutr 1992;11:701-706.
Gannon MC, Nuttall JA, Damberg G, Gupta V, Nuttall FQ: Effect of protein ingestion on the glucose appearance rate in people with type 2 diabetes. J Clin Endocrinol Metab 2001;86:1040-1047.
Rech ME: Observations on the decay of glycated hemoglobin HbA1c in diabetic patients. Exp Clin Endocrinol Diabetes 1996;104:102-105.
Yancy WS, Jr., Foy M, Chalecki AM, Vernon MC, Westman EC: A low-carbohydrate, ketogenic diet to treat type 2 diabetes. Nutr Metab (Lond) 2005;2:34 (7 pages).
Gannon MC: A computer program to calculate the rate of appearance of glucose in the peripheral circulation following infusion of labeled glucose. Copyright, University of Minnesota, Minneapolis, MN 1991 (27 pgs+1 title pg.).
Hamberg O, Vilstrup H: Effects of insulin and glucose on urea synthesis in normal man, independent of pancreatic hormone secretion. J Hepatol 1994;21:381-387.
Unger RH, Orci L: Physiology and pathophysiology of glucagon. Physiol Rev 1976;56:778-826.
Ahmed M, Nuttall FQ, Gannon MC, Lamusga RF: Plasma glucagon and alpha-amino acid nitrogen response to various diets in normal humans. Am J Clin Nutr 1980;33:1917-1924.
Nuttall FQ, Ngo A, Gannon MC: Regulation of hepatic glucose production and the role of gluconeogenesis in humans: is the rate of gluconeogenesis constant? Diabetes Metab Res Rev 2008;24:438-458.
Ahrens EH, Jr., Hirsch J, Oette K, Farquhar JW, Stein Y: Carbohydrate-induced and fat-induced lipemia. Trans Assoc Am Physicians 1961;74:134-146.
Barzel US, Massey LK: Excess dietary protein can adversely affect bone. J Nutr 1998;128:1051-1053.
Bonjour JP: Dietary protein: an essential nutrient for bone health. J Am Coll Nutr 2005;24:526S-536S.
Heaney RP: Protein intake and the calcium economy. J Am Diet Assoc 1993;93:1259-1260 (5 pages).
Cooper C, Atkinson EJ, Hensrud DD, Wahner HW, O'Fallon WM, Riggs BL, Melton LJ, 3rd: Dietary protein intake and bone mass in women. Calcif Tissue Int 1996;58:320-325.
Promislow JH, Goodman-Gruen D, Slymen DJ, Barrett-Connor E: Protein consumption and bone mineral density in the elderly : the Rancho Bernardo Study. Am J Epidemiol 2002;155:636-644.
Eastell R, Lambert H: Diet and healthy bones. Calcif Tissue Int 2002;70:400-404.
Roughead ZK, Johnson LK, Lykken GI, Hunt JR: Controlled high meat diets do not affect calcium retention or indices of bone status in healthy postmenopausal women. J Nutr 2003;133:1020-1026.
Wengreen HJ, Munger RG, West NA, Cutler DR, Corcoran CD, Zhang J, Sassano NE: Dietary protein intake and risk of osteoporotic hip fracture in elderly residents of Utah. J Bone Miner Res 2004;19:537-545.
Dawson-Hughes B, Harris SS, Rasmussen H, Song L, Dallal GE: Effect of dietary protein supplements on calcium excretion in healthy older men and women. J Clin Endocrinol Metab 2004;89:1169-1173.
Rizzoli R, Bonjour JP: Dietary protein and bone health. J Bone Miner Res 2004;19:527-531.
Accurso A, Bernstein RK, Dahlqvist A, Draznin B, Feinman RD, Fine EJ, Gleed A, Jacobs DB, Larson G, Lustig RH, Manninen AH, McFarlane SI, Morrison K, Nielsen JV, Ravnskov U, Roth KS, Silvestre R, Sowers JR, Sundberg R, Volek JS, Westman EC, Wood RJ, Wortman J, Vernon MC: Dietary carbohydrate restriction in type 2 diabetes mellitus and metabolic syndrome: time for a critical appraisal. Nutr Metab (Lond) 2008;5:9 (8 pages).
Westman EC, Yancy WS, Jr., Mavropoulos JC, Marquart M, McDuffie JR: The effect of a low-carbohydrate, ketogenic diet versus a low-glycemic index diet on glycemic control in type 2 diabetes mellitus. Nutr Metab (Lond) 2008;5:36 (9 pages).
Allick G, Bisschop PH, Ackermans MT, Endert E, Meijer AJ, Kuipers F, Sauerwein HP, Romijn JA: A low-carbohydrate/high-fat diet improves glucoregulation in type 2 diabetes mellitus by reducing postabsorptive glycogenolysis. J Clin Endocrinol Metab 2004;89:6193-6197.
Sharman MJ, Kraemer WJ, Love DM, Avery NG, Gomez AL, Scheett TP, Volek JS: A ketogenic diet favorably affects serum biomarkers for cardiovascular disease in normal-weight men. J Nutr 2002;132:1879-1885.

\* cited by examiner

COMPOSITIONS AND METHODS TO LOWER GLYCOHEMOGLOBIN LEVELS

CROSS-REFERENCE TO RELATED APPLICATIONS

The present application claims the benefit of U.S. Provisional Application Ser. No. 60/604,271, filed Aug. 25, 2004, which is hereby incorporated herein in its entirety by reference.

TECHNICAL FIELD

This invention relates to glycohemoglobin levels, and more particularly to a compositions and methods to lower glycohemoglobin levels.

BACKGROUND

The glucose absorbed following the ingestion of glucose-containing foods is largely responsible for a rise in the circulating glucose concentration. Dietary proteins, fats, and absorbed fructose and galactose resulting from the digestion of sucrose and lactose, respectively, have little effect on blood glucose concentration. Even short-term starvation (hours) results in a dramatic decrease in the blood glucose concentration in people with type 2 diabetes, which appears to be due largely to a rapid, progressive decrease in the rate of glycogenolysis.

SUMMARY

The invention provides for diets that significantly reduce the glycohemoglobin levels in individuals with type 2 diabetes. The diets can be provided to an individual in the form of cards and/or pages with an appropriate meal plan, food items and/or pre-packaged meals, or in an electronic medium for the individuals to use to develop appropriate meal plans. For example, one diet comprises food items having a nutritional composition that consists essentially of 30% protein, 50% fats, and 20% carbohydrates, while another diet comprises food items having a nutritional composition that consists essentially of 30% protein, 40% fats, and 30% carbohydrates.

In one aspect, the invention provides an article of manufacture that includes food items for a single meal or snack, for a single day, or for multiple days. In one embodiment of the invention, the food items have a nutritional composition that consists essentially of 30% protein, 50% fats, and 20% carbohydrates. Usually, the fats consist essentially of 10% saturated fats and 40% mono- and poly-unsaturated fats. In another embodiment, the food items have a nutritional composition that consists essentially of 30% protein, 40% fats, and 30% carbohydrates.

Generally, the food items can be breakfast food items, lunch food items, dinner food items, and/or snack food items. In some embodiments, the food items can be in a pre-packaged meal. Typically, the caloric value of the sum of the food items essentially equals the daily-recommended caloric intake for an individual. According to the invention, ingestion of such food items, for a period of about 3 weeks, by an individual having elevated glycohemoglobin levels, decreases glycohemoglobin levels in the individual. Such a decrease can be statistically significant.

In another aspect, the invention provides an article of manufacture that includes food items for multiple days. In one embodiment of the invention, a portion of the food items have a nutritional composition that consists essentially of 30% protein, 50% fats, and 20% carbohydrates and another portion of the food items have a nutritional composition that consists essentially of 30% protein, 40% fats, and 30% carbohydrates. This combination of diets can be further combined with food items that have a nutritional composition that consists essentially of 30% protein, 30% fats, and 40% carbohydrates. Alternatively, a portion of the food items have a nutritional composition that consists essentially of 30% protein, 30% fats, and 40% carbohydrates while a portion of the food items have a nutritional composition that consists essentially of 30% protein, 50% fats, and 20% carbohydrates. As another alternative, a portion of the food items have a nutritional composition that consists essentially of 30% protein, 30% fats, and 40% carbohydrates while a portion of the food items have a nutritional composition that consists essentially of 30% protein, 40% fats, and 30% carbohydrates.

In another aspect, the invention provides methods of reducing the level of glycohemoglobin in an individual. Such a method can include providing an article of manufacture that includes food items for a single day that have a nutritional composition that consists essentially of 30% protein, 50% fats, and 20% carbohydrates, and instructing the individual to consume the food items. Such instructions can be provided online or as written instructions accompanying the article of manufacture. Included in such a method, or as a separate method of reducing the level of glycohemoglobin in an individual, an article of manufacture can be provided that includes food items for a single day that have a nutritional composition that consists essentially of 30% protein, 40% fats, and 30% carbohydrates along with the appropriate instructions.

In yet another aspect, the invention provides methods of developing a meal plan for an individual having type 2 diabetes. Such a method includes providing the daily-recommended caloric intake for an individual; and selecting food items for the individual based on the individual's daily-recommended caloric intake. In an embodiment of the invention, the food items have a nutritional composition that consists essentially of 30% protein, 50% fats, and 20% carbohydrates. In another embodiment of the invention, the food items have a nutritional composition that consists essentially of 30% protein, 40% fats, and 30% carbohydrates.

Using these steps, a meal plan can be developed for the individual. The embodiments described herein can be used in combination. For example, one, two, or three weeks of food items that have a nutritional composition that consists essentially of 30% protein, 50% fats, and 20% carbohydrates, followed by one, two, or three weeks of food items that have a nutritional composition that consists essentially of 30% protein, 40% fats, and 30% carbohydrates.

According to the invention, ingestion of the food items does not result in ketosis in the individual, and results in maintenance of the individual's weight (i.e., does not result in the individual losing weight).

In still another aspect, the invention provides methods of developing a meal plan for an individual having type 2 diabetes. Such a method includes providing the daily-recommended caloric intake for an individual; and selecting food items for the individual based on the individual's daily-recommended caloric intake. In one embodiment of the invention, a portion of the food items have a nutritional composition that consists essentially of 30% protein, 50% fats, and 20% carbohydrates, and a portion of the food items have a nutritional composition that consists essentially of 30% protein, 40% fats, and 30% carbohydrates and/or 30% protein, 30% fats, and 40% carbohydrates. In another embodiment of the invention, a portion of the food items have a nutritional composition that consists essentially of 30% protein, 40% fats, and 30% carbohydrates, and a portion of the food items have a nutritional composition that consists essentially of 30% protein, 50% fats, and 20% carbohydrates and/or 30% protein, 30% fats, and 40% carbohydrates.

In yet another aspect, the invention provides a computer-readable storage medium having instructions stored thereon for causing a programmable processor to select a combination of food items for at least one day, wherein the food items collectively have a nutritional composition that consists essentially of 30% protein, 50% fats, and 20% carbohydrates or collectively have a nutritional composition that consists essentially of 30% protein, 40% fats, and 30% carbohydrates. The computer-readable storage medium, by instructing a programmable processor, can also select food items for individual meals, meals for a day or a number of days, or meals for one or more weeks that alternate or change between the two nutritional compositions set forth herein.

For example, a desired number of meals and snacks per day can be input into the processor; the weight and/or height of an individual can be input into the processor; the daily caloric intake of an individual can be input into the processor; and/or food item likes and/or dislikes can be input into the processor. The output is then the meal plans as described above. The output can be in any format including but not limited to print-outs, e-mails, and hyperlinks. The output can include a list of food item combinations for one or more meals or actual recipes for making such food items.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 2A shows the mean body weight on while on the control (open circles) or test diet (closed circles). FIG. 2B shows the plasma beta-hydroxybutyrate concentration after 5 weeks on the control (open circles) or test diet (closed circles).

FIG. 3A shows the mean plasma glucose concentration before (open triangles) and after (open circles) 5 weeks on the control diet. Insert: Net and total 24 hour integrated glucose area response. Area response was not significantly different. FIG. 3B shows the mean plasma glucose concentration before (closed triangles) and after (closed circles) 5 weeks on the test diet. Insert: Net and total 24 hour integrated glucose area response. Both the net and total area responses were significantly lower after the test diet ($p \leq 0.05$).

FIG. 4A shows the mean serum insulin concentration before (open triangles) and after (open circles) 5 weeks on the control diet. Insert: Net and total 24 hour integrated insulin area response. Area response was not significantly different. FIG. 4B shows the mean serum insulin concentration before (closed triangles) and after (closed circles) 5 weeks on the test diet. Insert: Net and total 24 hour integrated insulin area response. Both the net and total area responses were significantly lower after the test diet ($p \leq 0.05$).

FIG. 6A shows the mean plasma glucagon concentration before (open triangles) and after (open circles) 5 weeks on the control diet. Insert: Net and total 24 hour integrated glucagon area response. Area response was not significantly different. FIG. 6B shows the mean plasma glucagon concentration before (closed triangles) and after (closed circles) 5 weeks on the test diet. Insert: Net and total 24 hour integrated glucagon area response. The net and total area responses were significantly higher after the test diet ($p \leq 0.05$).

FIG. 7A shows the mean serum triacylglycerol concentration before (open triangles) and after (open circles) 5 weeks on the control diet. Insert: Net and total 24 hour integrated triacylglycerol area response. Area response was not significantly different. FIG. 7B shows the mean serum triacylglycerol concentration before (closed triangles) and after (closed circles) 5 weeks on the test diet. Insert: Net and total 24 hour integrated triacylglycerol area response. The total area response was significantly lower after the test diet ($p \leq 0.05$).

Like reference symbols in the various drawings indicate like elements.

DETAILED DESCRIPTION

To determine whether or not a diet low in food-derived glucose can lower both the fasting as well as the post-prandial blood glucose, a low carbohydrate diet was designed in which readily digestible starch-containing foods were de-emphasized. The carbohydrate content in the diet, however, was sufficient to prevent ketosis, which is in contrast to low-carbohydrate diets that are often advocated for weight loss. Glycohemoglobin, 24-hour glucose, insulin, C-peptide, beta-hydroxybutyrate, glucagon, triacylglycerol, and non-esterified fatty acids (NEFA) were examined to evaluate the effects of the diet on individuals with type 2 diabetes.

Blood Glucose, Glycohemoglobin and Type II Diabetes

Blood glucose levels represent the amounts of sugars present in the blood at the time the blood is withdrawn. Blood glucose levels vary throughout the day and depend upon diet, exercise, and the level of insulin in the blood. Individuals can test their own blood glucose levels using, for example, a home monitor or a hand-held meter.

The % total glycohemoglobin and the % hemoglobin $A_{1c}$ are two methods used to measure the glucose attached to hemoglobin. The % total glycohemoglobin used in this study is specific for the ketoamine adduct resulting from glucose attachment to primary amino groups on amino acids in the globin molecules in hemoglobin. Normally, only a small percentage of hemoglobin in the blood (~4% to 6%) has glucose bound to it. People with diabetes (or other conditions that increase their blood glucose levels), however, have a higher % glycohemoglobin than normal. The % glycohemoglobin is considered to be an index of the average, i.e. 24-hour integrated blood glucose concentration over an extended period of time, that of the life of the red blood cell (weeks to months). Thus, the % glycohemoglobin level is considered to represent the average blood glucose concentration in the weeks and months preceding the test. The glycohemoglobin level does not exhibit rapid changes due to exercise, medications, or eating prior to the test.

Diabetes and some of the risks of developing complications caused therefrom have been associated with the % glycohemoglobin. Diabetes is a chronic disease that develops when either the pancreas cannot produce enough insulin or the body cannot use insulin properly. Insulin allows sugar (e.g., glucose) to enter cells, where it is used for energy. Insulin also helps the body store extra glucose in muscle, fat, and liver cells. Symptoms of diabetes include increased thirst and frequent urination; unexplained increase in appetite; unexplained weight loss; fatigue; erection problems; blurred vision; and tingling or numbness in hands or feet. Individuals with diabetes have an increased risk for many serious health problems including hardening of the arteries (atherosclerosis) and heart problems, eye problems than can lead to blindness, circulation and nerve problems; and kidney disease or kidney failure. Type 2 diabetes can develop at any age, although it usually develops in adults. Type 2 diabetes used to be called adult-onset diabetes, as well as non-insulin-dependent diabetes mellitus (NIDDM) because it can often be treated without using insulin.

Diets Resulting in Low Biologically-Available Glucose

It has been determined and is described herein that an individuals' % glycohemoglobin level, plasma glucose level, serum insulin concentration, serum C-peptide concentration, and serum triacylglycerol level can be significantly reduced by following a diet that consists essentially of food items having a nutritional composition of approximately 30% protein, 50% fats, and 20% carbohydrate. This diet is referred to herein as "$Diet_{20}$." Such levels also can be significantly reduced by following a diet that consists essentially of food items having a nutritional composition of approximately 30% protein, 40% fats, and 30% carbohydrate. This diet is referred to herein as "$Diet_{30}$."

The desired nutritional composition described herein for $Diet_{20}$ or $Diet_{30}$ can be calculated for the meals in a single day, the meals in multiple days, the meals in one week, or longer. The diet of the invention usually uses the recommended daily caloric intake of an individual and the desired distribution of the food ingested in a day (e.g., the number of meals, and snacks, if desired) to determine the amount of food that should be ingested in each meal or snack in a day.

It may be impractical to achieve an exact percentage of each nutritional component in a food item, meal, or other diet constituent. It is understood by those of skill in the art that it is easier to calculate the desired nutritional composition in meals ingested over days or weeks than it is to calculate the desired nutritional composition over a single meal or the meals ingested in a single day. As such, it is to be understood that the percentage of components disclosed herein represents approximations attainable by a person of ordinary skill in the art using the nutritional guidelines provided herein for each diet. In addition, the diet provided herein may contain other components (e.g., nucleic acids, and/or medicaments) provided that these other components do not significantly alter the indicated nutritional composition of proteins, fats, and carbohydrates. This is what is meant by "consisting essentially of."

The $Diet_{20}$ and $Diet_{30}$ disclosed herein result in a statistically significant reduction in, for example, an individual's glycohemoglobin levels. As used herein, "statistically significant" refers to a p-value of less than or equal to 0.05, e.g., a p-value of less than or equal to 0.025 or a p-value of less than or equal to 0.01, using an appropriate measure of statistical significance, e.g., a two-tailed paired t-test.

A meal plan appropriately calculated for an individual using the $Diet_{20}$ or the $Diet_{30}$ described herein can be provided to an individual in need of such a diet in the form of cards or pages. The cards or pages can provide a list of food items and appropriate suggestions for meal combinations using such food items. The cards or pages also can provide a meal plan (i.e., suggested combinations of food items and meals for a given day) that meets both the caloric intake and nutritional composition requirements over the desired number of days or weeks. Recommended serving size can be indicated, and recipes for some of the food items or meal combinations can be provided, if desired.

A meal plan appropriately calculated for an individual using the $Diet_{20}$ or the $Diet_{30}$ disclosed herein also can be provided to an individual in the form of actual food items or pre-packaged meals. Food items can be packaged separately and ingested individually or combined by the individual into meals. As indicated above, suggestions for a variety of meals using combinations of the food items and pre-packaged meals that essentially meet the nutritional composition of the $Diet_{20}$ or $Diet_{30}$ and the caloric intake and the eating preferences of the individual can be provided. Pre-packaged meals are well known in the art and are routinely used in many types of diets, particularly those for the purpose of weight management. For example, sufficient food items and/or pre-packaged meals for multiple days (e.g., 7 days worth) or for one or more weeks (e.g., 2 weeks worth, or 1 month worth) can be provided to an individual.

In addition to the $Diet_{20}$ and $Diet_{30}$ disclosed herein, additional diets are disclosed that allow for ingestion of more carbohydrates and fewer fats, but that also reduce glycohemoglobin levels in an individual with elevated levels. For example, "$Diet_{40}$" is a diet in which food items having a nutritional composition that consists essentially of 30% protein, 30% fats, and 40% carbohydrates. $Diet_{20}$, $Diet_{30}$, and $Diet_{40}$ can be used in conjunction with one another (e.g., repeating schedule of 3-5 weeks on $Diet_{20}$, 2-3 weeks on $Diet_{30}$, and 2-3 weeks on $Diet_{40}$) to lower or maintain an individual's glycohemoglobin levels while consistently providing the individual with palatable and digestable food items and meals. It is apparent to those of skill in this art that the diet regimen an individual follows (e.g., which diet and for how long) will depend, in part, on the individual's ability to manage glycohemoglobin levels and/or the progression of the diabetes, while still taking into account the lipid profile of the individual.

Computer-Readable Medium for Implementing $Diet_{20}$ or $Diet_{30}$

Figure 1:
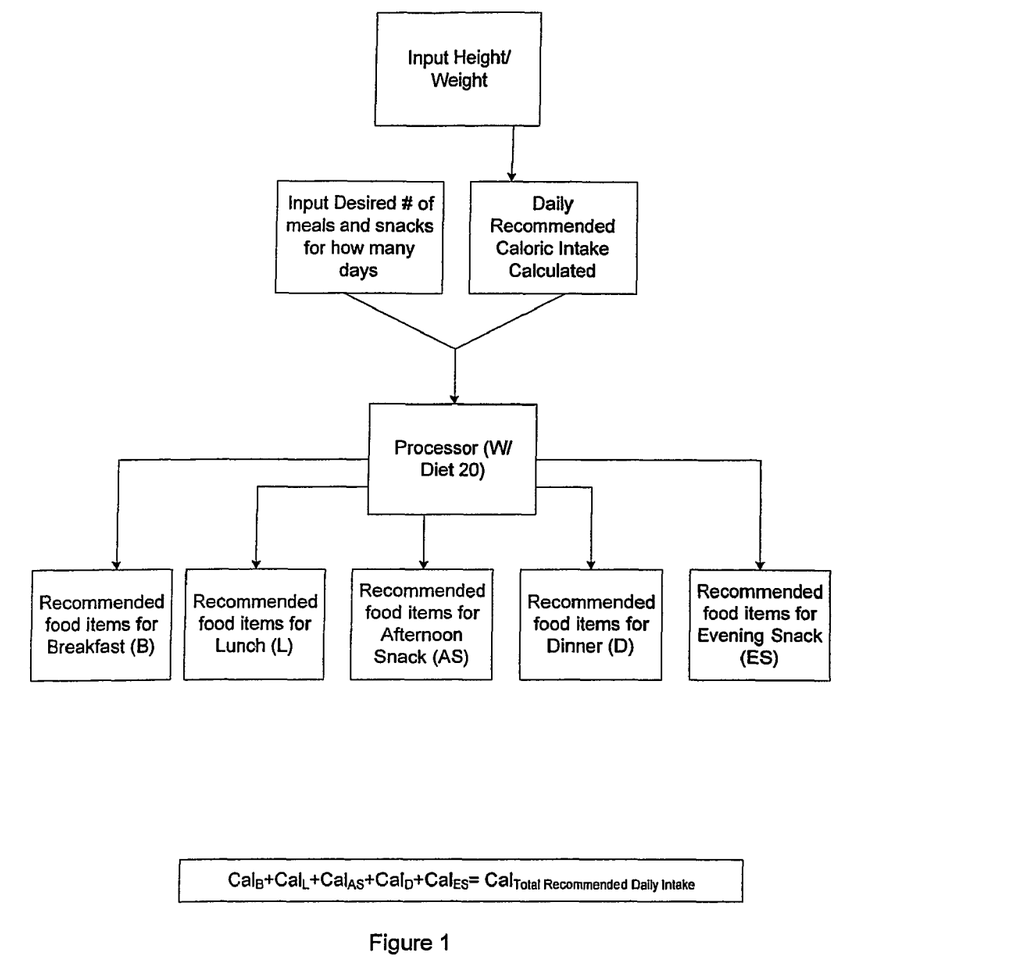
FIG. 1 shows an example of instructions for a processor to determine meal plans using the $Diet_{20}$ of the invention.

In addition to the cards, pages, recipes, meal plans, food items, and/or pre-packaged meals discussed above, the $Diet_{20}$ or $Diet_{30}$ described herein can be provided to an individual in the form of a computer-readable medium that contains instructions for causing a programmable processor to generate a meal plan for an individual that follows the $Diet_{20}$ or $Diet_{30}$. For example, a computer-readable medium containing instructions for generating a meal plan according to $Diet_{20}$ or $Diet_{30}$ can be provided to an individual in the form of, without limitation, a floppy disk, a CD, or a DVD. In addition, a computer-readable medium of the invention can be accessed electronically using, for example, a dial-up or internet connection to download or use remotely. FIG. 1 shows a chart of a representative processing system that can be used with a computer-readable medium of the invention to generate a meal plan according to the $Diet_{20}$ disclosed herein.

Instructions carried on a computer-readable medium of the invention can be implemented in a high level procedural or object oriented programming language to communicate with a processor. Alternatively, such instructions can be implemented in assembly or machine language, which can be compiled or interpreted. A processor can be a computer such as a personal computer or workstation that executes program code. One or more input devices (e.g., a keyboard or a mouse) and one or more output devices (e.g., a printer or a monitor) can be used in addition to the processor.

For example, an individual (or a representative of the individual, e.g., a nurse, a nutritionist, a dietician, etc.) can input the height (in inches and/or centimeters) and weight (in pounds and/or kilograms) of the individual. Age and gender also can be input, but are not necessary. The daily caloric intake can take into account an individual's activity level and/or weight goals, although neither the $Diet_{20}$ nor the $Diet_{30}$ described herein are intended for weight loss purposes. For example, individuals can indicate if they consider themselves to be sedentary, or to have minimal, moderate, or strenuous activity during the day, and whether they wish to maintain their weight, lose weight, or gain weight. From this information, an individual's recommended daily caloric intake can be determined. Alternatively, a desired daily caloric intake, if known, can be input directly.

The individual then can input the number of meals they wish to ingest in a day. Some individuals prefer to eat three meals a day, while others prefer to include snacks between one or more meals. The preference for the number of meals and snacks in a day can be used to determine the caloric distribution during the day.

The instructions contained on a computer-readable medium of the invention also can allow for a variety of specialized options. For example, individuals can select (or deselect) food items that the individual likes or dislikes, or cannot eat, for example, due to allergies, religious beliefs/practices, or adverse reactions with a medication. The instructions contained on a computer-readable medium of the invention can include a system of equivalents such that foods that are removed due to, for example, one of the previously-discussed reasons, can be substituted with food items having a similar caloric and nutritional value as the food removed. In addition, the instructions on the computer-readable medium can allow for input of the number of people for which a recipe will be prepared, the time frame for which the individual wants to spend preparing a food item, and/or a choice of the ethnicity of a food item or meal (e.g., Chinese, Italian, or Mexican).

As part of the invention, there is provided a database containing the nutritional composition of a variety of food items and meals. Such a database can be contained on the same or on a different computer-readable medium as the instructions for determining the $Diet_{20}$ or $Diet_{30}$ meal plan, or can be accessed and/or downloaded via, for example, an internet connection. The database provides a large number of food items and meals that can be mixed and matched in combination to result in a variety of meals and snacks having the appropriate nutritional composition and caloric values.

In accordance with the present invention, there may be employed conventional laboratory and/or clinical testing techniques within the skill of the art. Such techniques are explained fully in the literature. The invention will be further described in the following examples, which do not limit the scope of the invention described in the claims.

EXAMPLES

A. $Diet_{20}$

Example 1

Participants

Male subjects with mild, untreated type 2 diabetes were studied in a "Special Diagnostic and Treatment Unit" (SDTU), a facility similar to a Clinical Research Center. All subjects met the National Diabetes Data Group criteria for the diagnosis of type 2 diabetes mellitus (Report of the Expert Committee on the Diagnosis and Classification of Diabetes Mellitus: *Diab. Care,* 21:S5-S19 (Suppl 11), 1998). Subject characteristics are given in Table 1. The study was approved by the Department of Veterans Affairs Medical Center and the University of Minnesota Committees on Human Subjects and written informed consent was obtained from all subjects. The subjects did not have hematologic abnormalities, kidney disease, liver disease, macroalbuminuria (>300 mg/24 h), congestive heart failure, or untreated thyroid disease. Prior to the study, all subjects were interviewed to determine their physical activity profile, food aversions, and to explain the study process and commitment in detail. Subjects confirmed they had been weight stable for at least 3 months. They were instructed to maintain their current activity level throughout the study. Two weeks prior to beginning the study, the subjects completed a 3-day food frequency questionnaire with one of the days being a Saturday or Sunday. This information was used to calculate the total food energy necessary to maintain body weight. None of the subjects was being treated with oral hypoglycemic agents or insulin at the time they were enrolled in the study. A 5-week randomized, crossover study design was used with a 5-week washout period between diets.

TABLE 1

| | | | | | | | | |
|---|---|---|---|---|---|---|---|---|
| Patient characteristics | | | | | | | | |
| Patient | Age (yrs) | Height [inches (cm)] | Weight [pounds (kg)] | BMI (kg/m²) | tGHb (%) | Duration of diabetes (months) | Concomitant diseases | Medications |
| 1 | 69 | 74 (188) | 221 (100) | 27 | 8.7 | 60 | hypertension, dyslipidemia, coronary heart disease | simvastatin, lisinopril, rabeprazole, ASA |
| 2 | 72 | 69 (165) | 239 (109) | 35 | 10.0 | 12 | chronic obstructive | terazosin |

TABLE 1-continued

Patient characteristics

| Patient | Age (yrs) | Height [inches (cm)] | Weight [pounds (kg)] | BMI (kg/m$^2$) | tGHb (%) | Duration of diabetes (months) | Concomitant diseases | Medications |
|---|---|---|---|---|---|---|---|---|
| 3 | 51 | 68 (173) | 181 (82) | 27 | 8.6 | 12 | pulmonary disease none | ASA, naproxen |
| 4 | 66 | 72 (183) | 196 (89) | 27 | 9.0 | 180 | hypertension | none |
| 5 | 82 | 71 (180) | 204 (93) | 28 | 11.2 | 48 | none | lisinopril, ASA |
| 6 | 56 | 72 (183) | 267 (121) | 35 | 10.1 | 24 | obesity, dyslipidemia | none |
| 7 | 51 | 66 (168) | 195 (89) | 31 | 10.0 | 14 | none | ASA, naproxen |
| 8 | 59 | 67 (170) | 233 (106) | 36 | 9.4 | 19 | hypertension, obesity | lisinopril |
| Mean | 63.3 | 70 (176) | 217 (99) | 31 | 9.6 | 46 | — | — |
| Range | 51-82 | 66-74 (168-188) | 181-267 (82-121) | 27-36 | 8.6-11.2 | 12-180 | — | — |

Example 2

Diet

The control diet was designed according to the recommendations of the American Heart Association (American Heart Association: *Dietary guidelines for healthy American adults; a statement for physicians and health professionals by the Nutrition Committee, Circulation*, 74: 1465A-1468A, 1986), and the United States Department of Agriculture (USDA: *The food guide pyramid*, Washington D.C., US Government Printing Office, 1992; USDA & US Department of Health and Human Services: *Nutrition and your health: dietary guidelines for Americans*, Washington D.C., US Government Printing Office, 1995). The control diet consisted of 55% carbohydrate, with an emphasis on starch-containing foods, 15% protein, and 30% fat (10% monounsaturated, 10% polyunsaturated, 10% saturated fatty acid content). The control diet is a diet that is recommended for the general population as a means of reducing one's risk for coronary heart disease.

The low-biologically-available-glucose diet (the "test" diet) was designed to have a nutritional composition that consists essentially of 30% protein, 50% fats, and 20% carbohydrate. The saturated fatty acid content of the test diet was ~10% of total food energy, thus the majority of the fat was mono- and polyunsaturated fats. The nutritional composition of the control and test diets is given in Table 2, and Table 3 shows representative meals for the control and test diet.

TABLE 2

Composition of diets

| | Control Diet | Test Diet |
|---|---|---|
| Energy (kcal) | 2,825 | 2,825 |
| Protein [g (%)] | 106 (15) | 210 (30) |
| Carbohydrate [g (%)] | 388 (55) | 142 (20) |
| Monosaccharides (g) | 64 | 31 |
| Disaccharides (g) | 50 | 16 |
| Fat [g (%)] | 94 (30) | 158 (50) |
| Monounsaturated (g) | 29 | 62 |
| Polyunsaturated (g) | 24 | 35 |
| Saturated (g) | 33 | 30 |
| Cholesterol (mg) | 375 | 441 |
| Dietary fiber (g) | 24 | 36 |

TABLE 3

Sample Menu for One Day

| Control | Diet$_{20}$ |
|---|---|

Breakfast

| | |
|---|---|
| 57 g (2 oz) Total Cereal | 124 g (4 oz) Egg Substitute |
| 50 g (2 slice) Wheat Bread | 23 g Green Pepper |
| 244 g (1 Cup) 2% Milk | 56 g (2 oz) Cheddar Cheese |
| 10 g (2 tsp) Margarine | 18 g (1 slice) Tomato |
| 10 g (2 tsp) Jelly | 131 g (1) Fresh Orange |
| 114 g (1) Banana | |
| 120 g (4 oz) grape Jelly | |
| 8 g (2 tsp) Sugar | |

Lunch

| | |
|---|---|
| 50 g (2 slices) Wheat Bread | 226 g (8 oz) Roasted Ham |
| (3 oz) Lean Ham | 85 g (3 oz) Swiss Cheese |
| 5 g (1 Tsp) Mustard | 90 g (1 Small) Tomato |
| (2 oz) Lite Cheese | 28 g (2 Tbsp) Mayonnaise |
| 10 g (2 Tsp) Margarine | 5 g (1 Tsp) Mustard |
| 5 g (1) Radish | 7 g Lettuce Leaves |
| 36 g (4) Carrot Sticks | 253 g (1 Cup) Split Pea Soup |
| 50 g (4) Celery Sticks | 20 g (3) Rye Krisp |
| 166 g (1) Fresh Pear | |
| 21 g (7) Vanilla Wafers | |

Snack

| | |
|---|---|
| 72 g (30) Grapes | None |
| 58 g (1) Banana Nut Muffin | |
| 5 g (1 Tsp) Margarine | |

Dinner

| | |
|---|---|
| 135 g (1 Cup) Green Beans | 50 g (½ Stalk) Raw Celery Sticks |
| 25 g (1 slice) Wheat Bread | 170 g (6 oz) Tuna |
| 15 g (1 Tbsp) Margarine | 55 g (4 Tbsp) Mayonnaise |
| 138 g (1) Apple | 80 g (½ Cup) Peas |
| 28 g (2) Fig Newtons | 138 g (1) Raw Apple |

TABLE 3-continued

Sample Menu for One Day

| Control | Diet$_{20}$ |
|---|---|
| 41 g (¾ Cup) Lettuce | |
| 45 g (½ Tom) Tomato Wedges | |
| 15 g (1 Tbsp) Reg Italian Dressing | |
| 113 g (4 oz) Lean Pork Roast | |
| 160 g (1 Cup) Cooked Noodles | |

Snack

| | |
|---|---|
| 57 g (2 oz) American Cheese | 56 g (2 oz) Dry Roasted Peanuts |
| 17 g (6) Saltine Crackers | |

The distribution of total food energy intake for the control diet was about: 24% for breakfast, 27% for lunch, 9% for the 1600-hour snack, 32% for supper, and 8% for the 2100-hour snack. For the Diet$_{20}$, the distribution was about: 17% for breakfast, 38% for lunch, 32% for supper, and 12% for the 2100-hour snack. The amount of carbohydrate in the meals and snacks for the control diet was approximately 113 g for breakfast, 79 g for lunch, 38 g for the 1600-hour snack, 109 g for dinner and 34 g for the 2100-hour snack (total of 373 g CHO); for the Diet$_{20}$, it was approximately 25 g for breakfast, 53 g for lunch, 42 g for dinner and 21 g for the 2100-hour snack (total of 141 g CHO).

Example 3

Experimental Plan

Subjects were randomized to begin the study with either the test diet or the control diet by a flip of a coin. Six subjects started on the test diet, five subjects started on the control diet. Unfortunately, three of the subjects started on the control diet did not complete the study for personal reasons. Therefore, the data are presented on 8 subjects who completed both arms of the study. Subjects were admitted to the SDTU on the evening prior to the study. The following day, standardized meals containing 55% carbohydrate, 30% fat, and 15% protein (essentially the same as the control diet) were given to all subjects for breakfast, lunch and dinner, at 0800 h, 1200 h, and 1800 h. Subjects were asked to remain in the SDTU during the study period with minimal activity.

On the second day in the SDTU, standardized meals again were given. This diet was similar for both baseline studies and was referred to as "pre-control" and "pre-test" diets depending on which study diet followed the inpatient stay. In addition to the 0800 h, 1200 h and 1800 h meals; snacks were given at 1600 h and 2100 h. Blood was obtained fasting at 0730 h, 0745 h and 0800 h, every 15 minutes for the first hour after meals, every ½-hour for the next two hours, and then hourly until the next meal. Blood was drawn at a total of 46 time points. Following this 24-hour data accumulation period, the subjects were sent home with all the necessary food for the next 2-3 days as appropriate for the diet to which they were randomized.

Subjects returned to the SDTU every 2-3 days to pick up food and meet with the study dietitian. At that time, subjects provided a urine specimen for analysis of creatinine and urea to determine dietary compliance. Subjects were weighed and had blood pressure, total glycohemoglobin, and blood glucose measured. If their body weight decreased or increased on two successive occasions, the total food energy of the meals was increased or decreased as appropriate to attempt to maintain weight stability throughout the study. In addition, subjects were interviewed regarding dietary compliance, and questions or concerns about the study. At the end of the 5-week period, the subjects again were admitted to the SDTU and blood was drawn over a 24-hour period of time as described above. During this time, the test or control meals were continued for each appropriate group. Following this 24-hour data accumulation period, the subjects were sent home to consume a diet of their choice, i.e., their usual diet, for the following ~5 weeks. This was the washout period.

Example 4

Biological Measurements

The plasma glucose concentration and beta-hydroxybutyrate concentration were determined by enzymatic methods using an Analox analyzer with an $O_2$ electrode (Analox Instruments, Ltd; London, UK). Total glycohemoglobin was measured by boronate affinity HPLC (BioRad Variant, Bio-Rad Labs, Inc.; Hercules, Calif.). Serum immunoreactive insulin was measured using a standard double-antibody radioimmunoassay (RIA) method using kits produced by Incstar (Stillwater, Minn.). Glucagon and C-peptide were measured by RIA using kits from Linco Research (St. Louis, Mo.) and Diasorin (Stillwater, Minn.), respectively. NEFAs were measured enzymically using a kit manufactured by Wako Chemicals, Inc. (Richmond, Va.). Weight was determined in street clothes without shoes on a digital scale (Scalitronix, White Plains, N.Y.). Blood pressure was measured using a Dinemap instrument (Critikon/Mediq, Pennsauken, N.J.).

The total α-amino nitrogen concentration was determined by the method of Goodwin, which is a measure of the total amino acid concentration. The plasma TSH (Abbott Architect; Abbott Park, Ill.), GH (Quest; New Brighton, Minn.), B12 and folate (Diagnostic Products Corp.; Los Angeles, Calif.) were determined by chemiluminescence. Total T3 and free T4 were determined by Chemiflex (Abbott Architect). IGF-1 was determined by RIA (Quest). Homocysteine was measured by HPLC (Hewlett Packard, Palo Alto, Calif.). The plasma and urine creatinine, urea nitrogen and uric acid were measured by an automated method on an OrthoClinical diagnostic Vitros 950 analyzer (Raritan, N.J.). Microalbumin was determined using a Beckinan-Coulter array 360 analyzer (Fullerton, Calif.). Urinary free cortisol was determined in the laboratory of Dr. B. Pearson-Murphy using an HPLC purification step followed by a cortisol binding assay. Urinary aldosterone was determined by RIA (Diagnostic Products Corp.). Urinary calcium and magnesium were measured colorimetrically on a J&J Vitros Instrument (J&J Engineering; Poulsbo, Wash.). Qualitative urinary ketones were measured with a Ketostix (Bayer Corporation; Elkhart, Ind.).

The total amount of protein oxidized was determined by quantifying the urine urea nitrogen excreted over the 24 hours of the study in association with the change in the amount of urea nitrogen retained endogenously. The latter was calculated by determining the change in plasma urea nitrogen concentration between the fasting baseline and at the end of the 24-hour study period, and correcting for plasma water by dividing by 0.94. In this calculation, it is assumed that there is a relatively rapid and complete equilibration of urea in total body water. Total body water as a percentage of body weight was calculated as previously described (Watson et al., 1980, *Am. J. Clin. Nutr.*, 33:27-39). The overall assumption is that a change in plasma urea concentration is indicative of a corresponding change in total body water urea concentration. In this 24-hour study, the beginning and ending urea nitrogen concentrations were essentially identical, indicating no retention of urea. The sum of total urea nitrogen in urine and body water was divided by 0.86 to account for 14% lost to metabolism in the gut.

The net 24-hour incremental area responses were calculated using the overnight fasting value as baseline. Total 24-hour area responses were calculated using zero as the baseline. Both area calculations were done using a computer program based on the trapezoid rule. Statistics were determined using Student's t test for paired variates, with the Statview 512+ program (Brain Power, Calabasas, Calif.) for the Macintosh computer (Apple Computer, Cupertino, Calif.). A p value of <0.05 was the criterion for significance. Data are presented as the mean±SEM, unless otherwise indicated.

Example 5

Results #1

The average body weight was 219±10 lbs (99±4.5 kg) and 216±10 lbs (98±4.5 kg) at the beginning of the control and test diets, respectively. At the end of the 5 weeks on the control diet, the average body weight was 215±10 lbs (98±4.5 kg). Following 5 weeks on the test diet, the average weight was 212±9 lbs (96±4.1 kg). Thus, the average body weight decreased by 4 pounds (1.8 kg) during the 5-week study period, regardless of diet (FIG. 2A).

Urine ketones were monitored twice weekly while subjects were on the test diet. They were always zero to trace using nitroprusside impregnated Ketostix (Bayer Corporation, Elkhart, Ind.). Twenty-four hour urine ketones were identical at the beginning and end of the test diet (196±8 μmol/L and 196±9 μmol/L respectively). Before and after the control diet, they were 187±7 μmol/L and 203±10 μmol/L, respectively.

Figure 2:
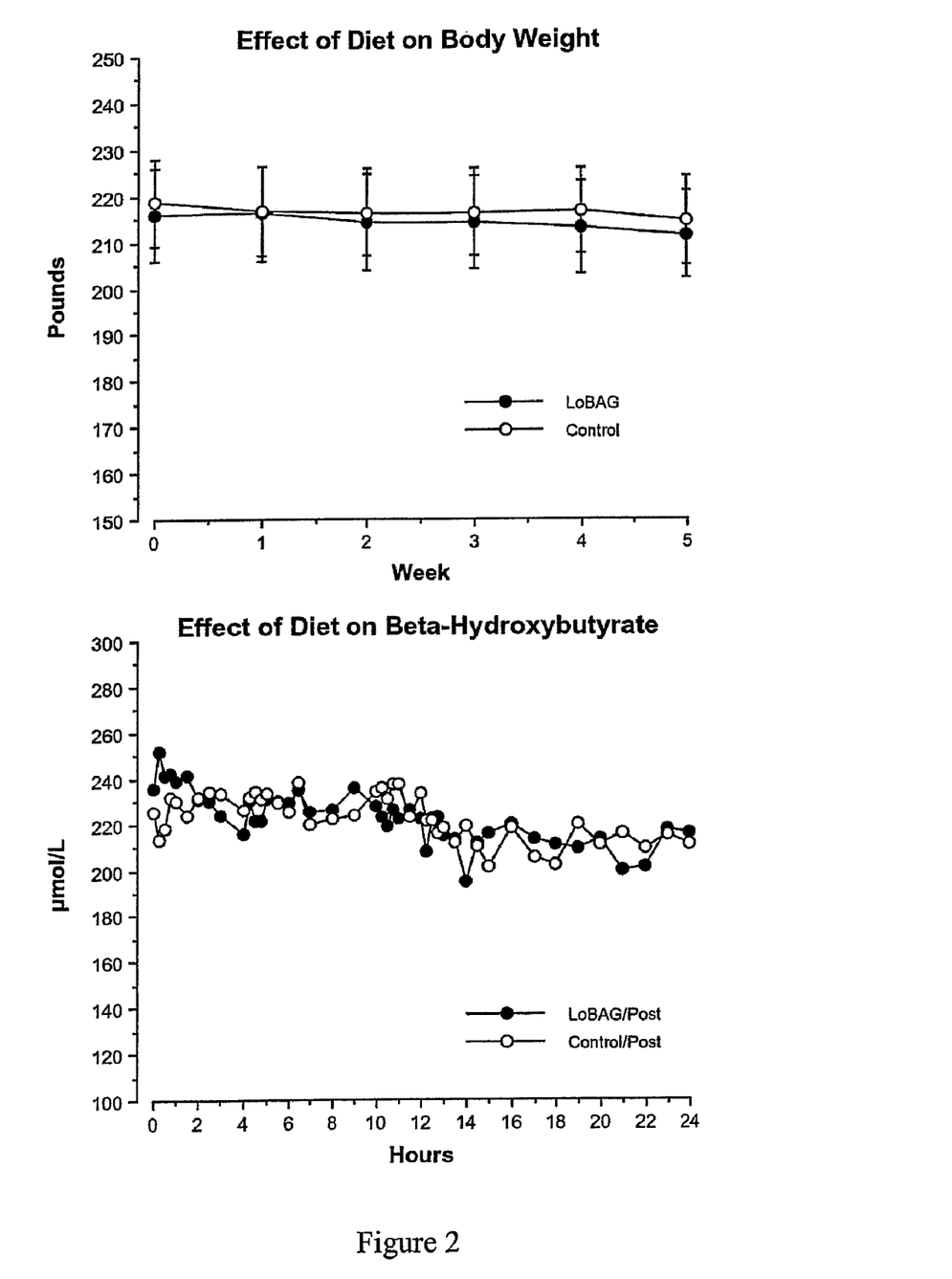
FIG. 2 depicts graphs.

The mean fasting β-hydroxybutyrate concentration was 225±15 μmol/L after five weeks on the control diet (FIG. 2B). Following five weeks on the test diet, the mean fasting concentration was 236±27 μmol/L. The 24-hour profiles were similar when the subjects ingested either the control or the test diet.

The mean fasting glucose concentration prior to starting the control diet was 180±10 mg/dl (10±0.6 mmol/L) (FIG. 3A). After five weeks on the control diet, the fasting glucose concentration was decreased to 159±11 mg/dl (8.8±0.6 mmol/L), but this was not significant (p=0.66). Prior to starting the test diet the mean fasting glucose concentration was 167±13 mg/dl (9.3±0.7 mmol/L), similar to that prior to starting the control diet (p=0.24). After 5 weeks on the test diet, the fasting glucose concentration was significantly decreased to 119±7 mg/dl (66±0.4 mmol/L) (p<0.003) (FIG. 3B).

Figure 3:
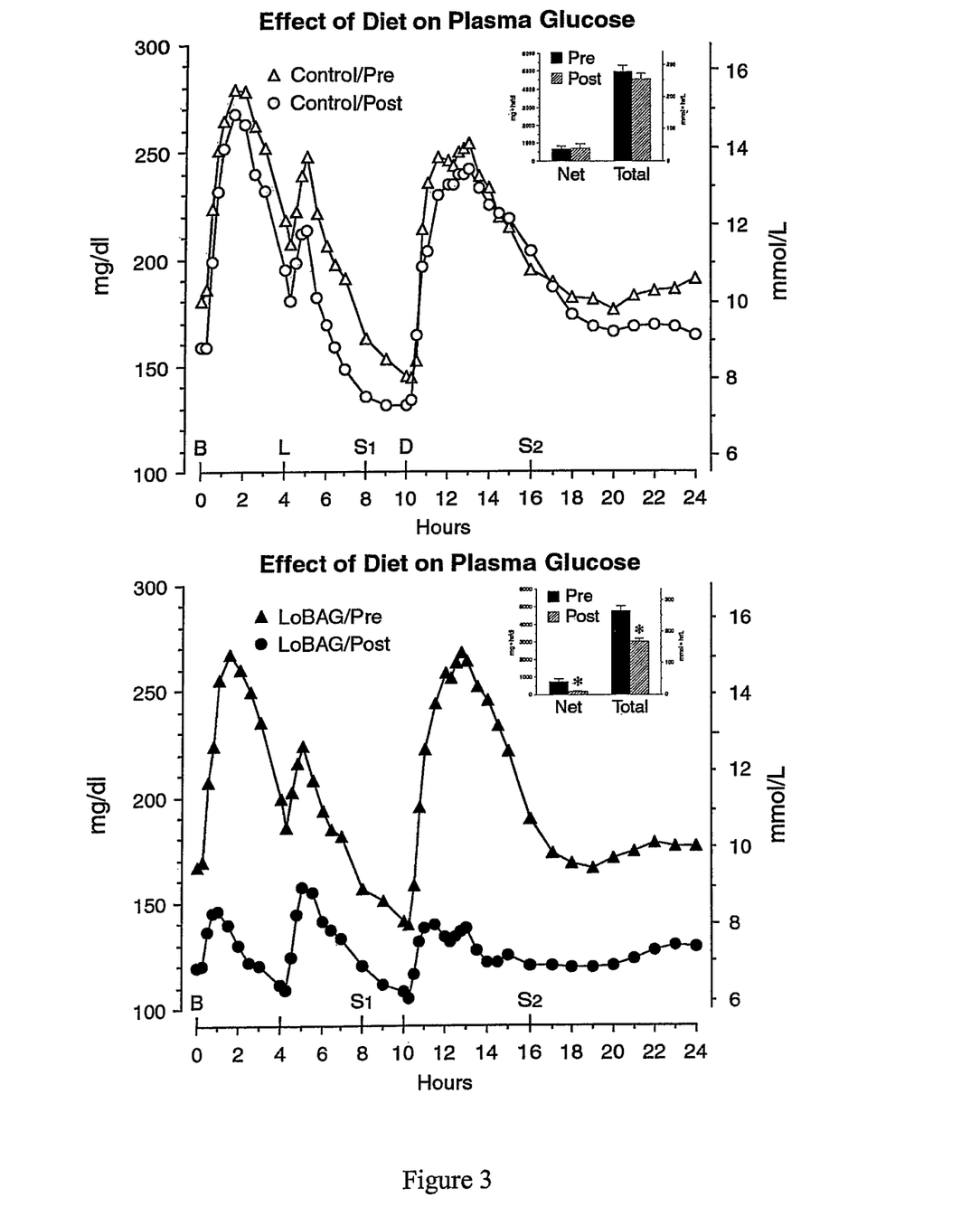
FIG. 3 depicts graphs.

The mean 24-hour integrated net glucose area responses were similar for the pre-control, pre-test and post-control diets (681±174, 731±159 and 730±236 mg·h/dl [38±9.7, 41±8.8, 41±13.1 mmol·hr/L], respectively) (FIG. 3, insets, left bars). Following five weeks on the test diet, the net mean 24-hour integrated glucose area response was decreased by 77% (165±59 mg·h/dl) (9.2±3.3 mmol·hr/L) p<0.02).

Total 24-hour integrated glucose area responses also were similar for pre-control, pre-test and post-control diets (4998±337, 4746±301 and 4554±347 mg·h/dl [278±18.7, 264±16.7, 253±19.3 mmol·hr/L], respectively) (FIG. 3, insets, right bars). The total area response following 5 weeks on the test diet was decreased significantly (3023±160 mg·h/dl) (168±8.9 mmol·hr/L) (p<0.0004 compared to the 5-week post-control and p<0.0001 compared to pre-test). Based on these integrated areas, the mean glucose concentration over the 24 hour periods of study was reduced from 198 mg/dl to 126 mg/dl (11 mmol/L to 7 mmol/L) after 5 weeks on the test diet, a 36% decrease (p<0.0001).

The mean fasting insulin concentrations before and after 5 weeks on both the control and test diets were identical (12±2 μU/ml) (72±12 pmol/L) (FIGS. 4A and 4B).

Figure 4:
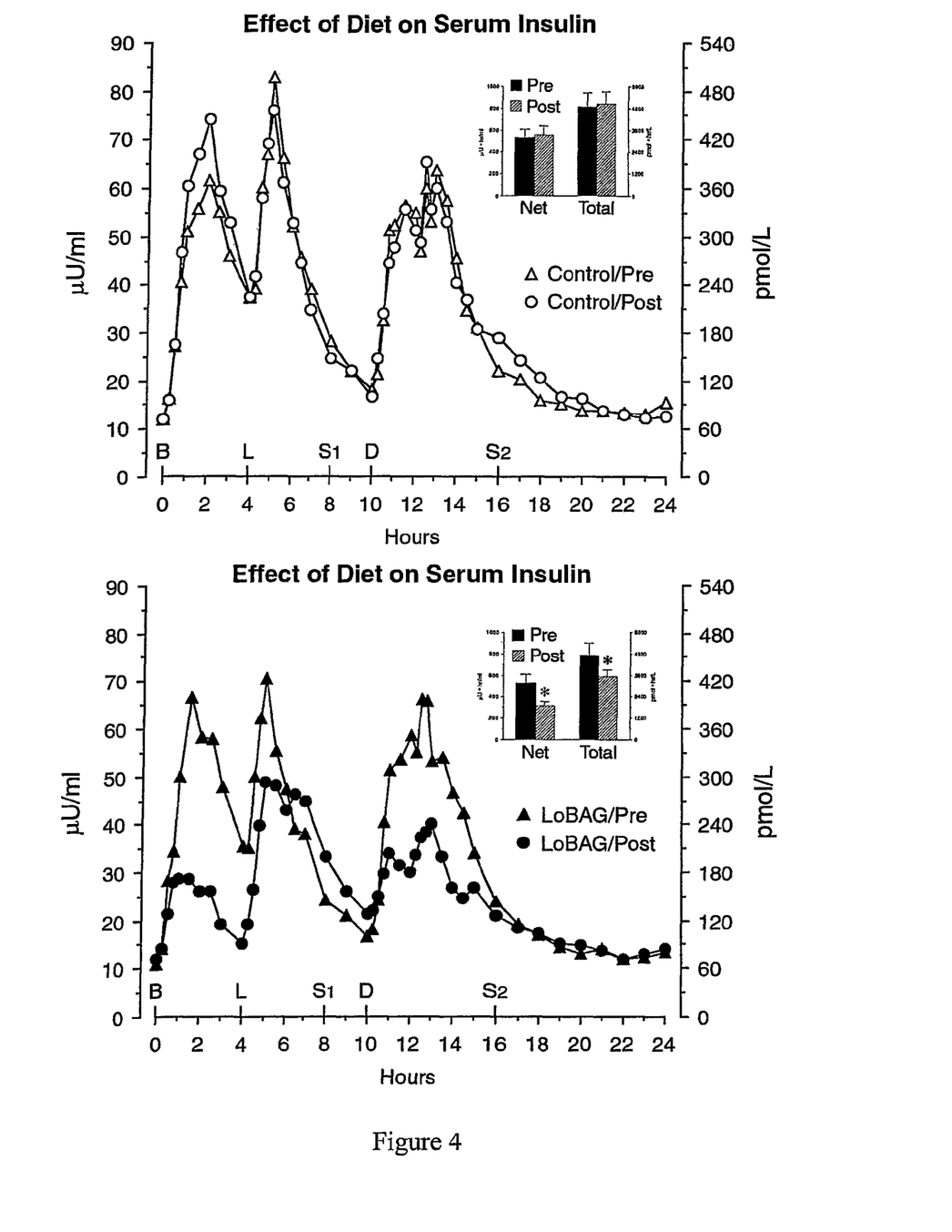
FIG. 4 depicts graphs.

The mean 24-hour integrated insulin area response above the fasting value was similar following the pre- and post-control diet and pre-test diet (534±73 μU·h/ml; 554±84 μU·h/ml; and 530±81 μU·h/ml [3024±438, 3324±504, 3180±486 pmol/L], respectively) (FIG. 4, insets). It was decreased at five weeks on the test diet (318±39 μU·h/ml) (1908±702 pmol/L). This was a decrease of 40% from the pre-test value (p<0.01) (FIG. 4, insets). The mean 24-hour total integrated insulin area response decreased by 25%.

The mean fasting C-peptide concentration before and after the control diet was 0.86±0.08 and 0.91±0.08 pg/ml, and 0.81±0.09 and 0.92±0.08 before and after the test diet. The 24-hour time course response was similar to the insulin response. The net C-peptide area response was decreased by 34% after 5 weeks on the test diet. This was statistically significant (p<0.05).

Figure 5:
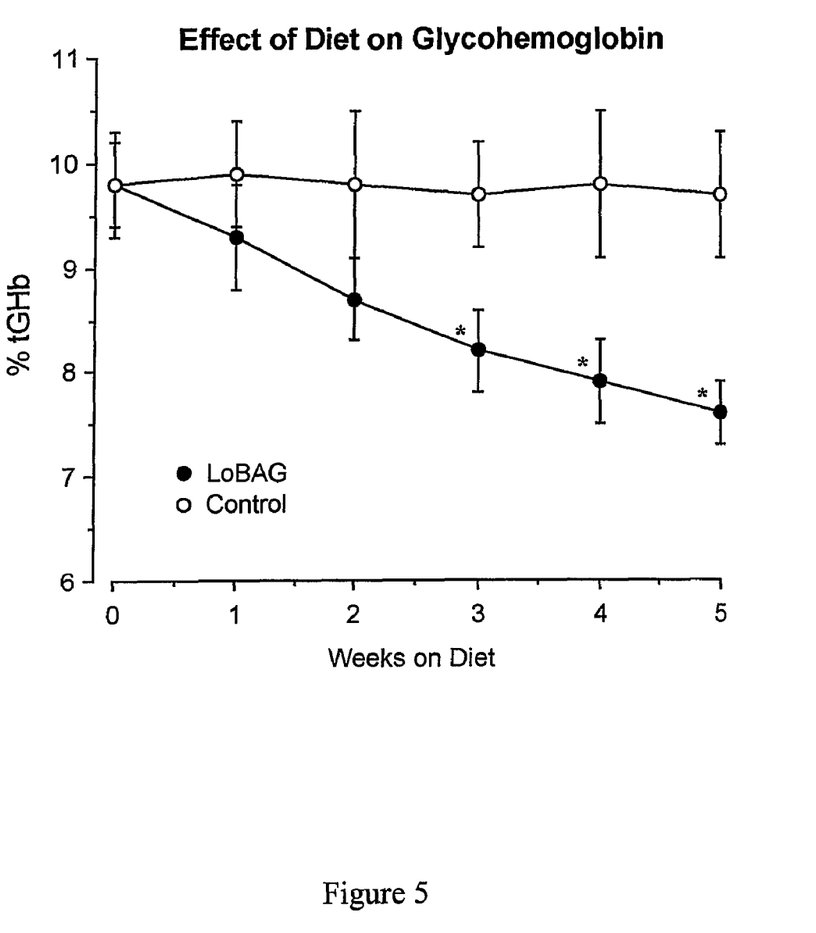
FIG. 5 shows the mean total glycohemoglobin response during the 5 weeks of the control (open circles) or test diet (closed circles). The tGHb on the test diet was significantly lower at weeks 3, 4, and 5 compared to the control diet ($p \leq 0.05$).

The mean total glycohemoglobin was essentially unchanged during the 5 weeks on the control diet (FIG. 5). A decrease in total glycohemoglobin was present 1 week after the institution of the test diet, and became significant after 3 weeks on the test diet. At the end of the 5-week period, the total glycohemoglobin had decreased 22%, from 9.8±0.5% to 7.6±0.3% (p<0.0007).

Figure 6:
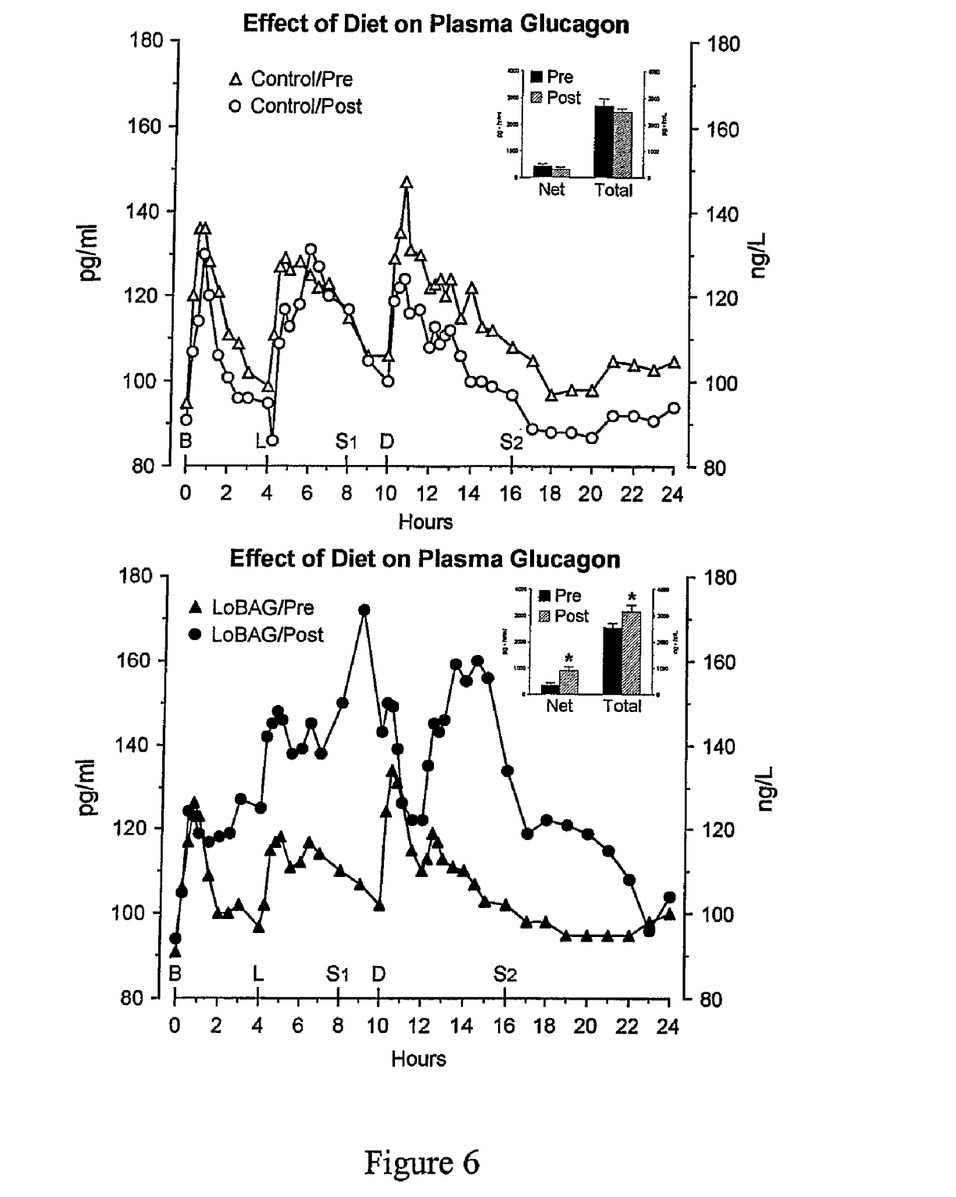
FIG. 6 depicts graphs.

The mean fasting glucagon concentrations were similar before and after both the control and test diets (95±11, 91±8, 91±7, and 94±7 pg/ml, respectively) (FIGS. 6A and 6B). After 5 weeks on the test diet, the glucagon response was similar to the control for the first hour after breakfast. Subsequently, the glucagon concentration was higher at every time point until 0700 hr the following morning, except for one time point after dinner. Both the net and the total glucagon area responses were significantly increased after the test diet (p<0.05) (FIG. 6, insets).

The mean fasting NEFA concentrations were 765±67, 654±59, 718±70 and 593±50 μEq/l, before and after the control and test diets, respectively. These differences were not statistically significant p>0.05). The 24-hour excursions were similar on the pre-control and pre-test diet days. When the test diet was ingested, the fasting NEFA was lower, the increase after the lunch meal was attenuated, as was the decrease before dinner. The rise after dinner was more rapid and reached a higher concentration.

The mean 24-hr integrated net NEFA area responses were (−)5323±1187, (−)2468±693, (−)4525±1660 and 80±1809 μEq hr/l before and after the control and test diets, respectively. The small positive area response after the test diet was statistically significantly different compared to the response before the test diet (p<0.05). Total areas were not statistically different from one another.

The mean fasting triacylglycerol concentrations were 264±36, 226±32, 246±27 and 149±23 mg/dl before the after the control and test diets, respectively. The fasting triacylglycerol concentration was significantly lower after 5 weeks on the test diet (p<0.05). After ingestion of either diet, the triacylglycerol concentration increased until ~1200-1400 h, decreased at 2000-2200 h, increased slightly at ~2400 h and subsequently returned to the fasting value by 0800 h the following morning.

Figure 7:
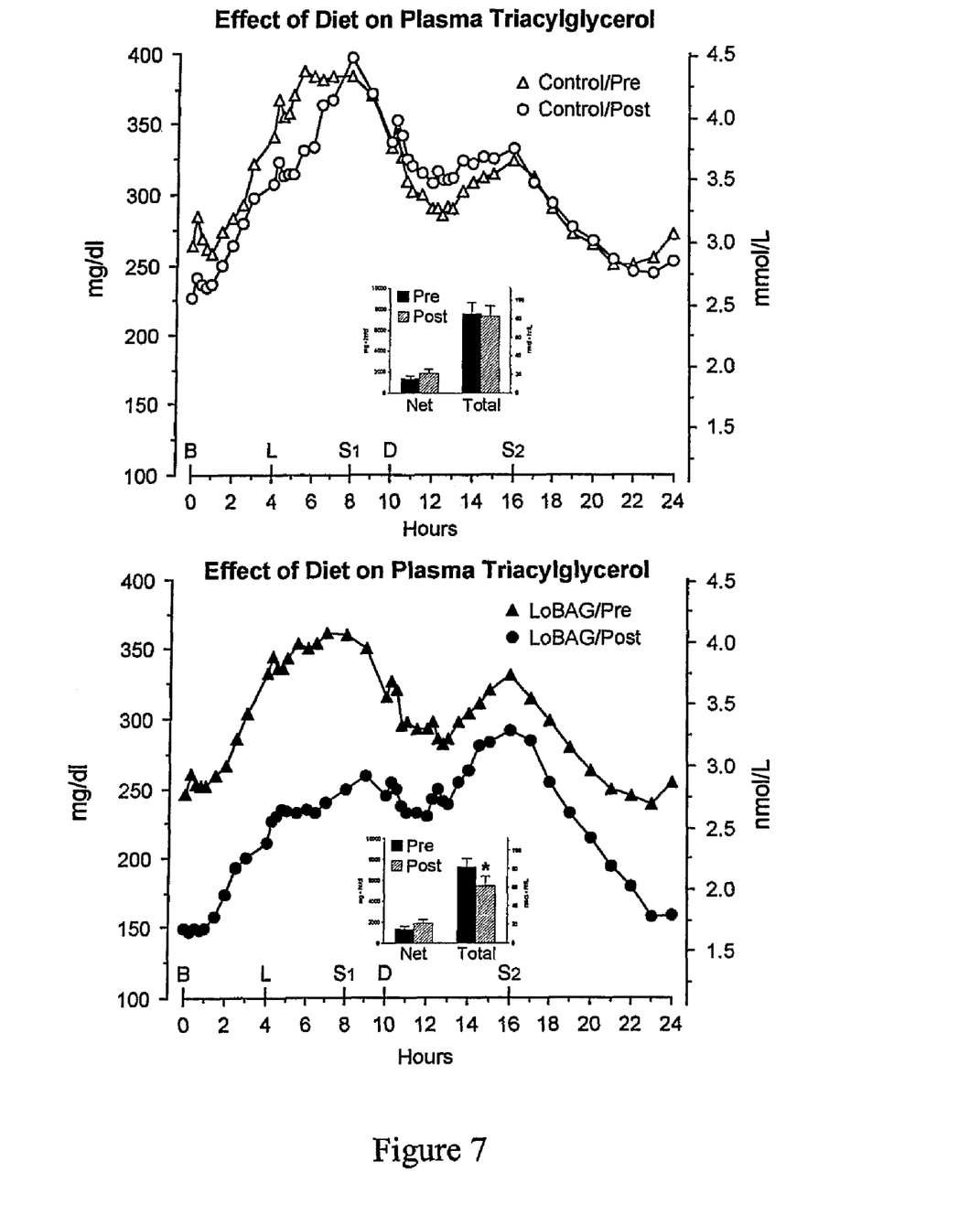
FIG. 7 depicts graphs.

The mean 24-h integrated net triacylglycerol area response was not significantly different between diets. However, the mean 24-h integrated total area response was significantly lower after 5 weeks on the test diet (p<0.05) (FIG. 7, insets).

The total cholesterol concentrations were 195±7, 184±17, 188±10 and 177±8 mg/dl before and after the control and test diets, respectively. The LDL-cholesterol concentrations were 105±9, 102±2, 105±7, and 110±6 mg/dl before and after the control and test diets, respectively. The HDL-cholesterol concentrations were 38±1, 37±2, 37±2, and 36±2 before and after the control and test diets, respectively. The total, LDL, and HDL concentrations were not significantly different between diets or before and after each diet.

The serum total, LDL, and HDL cholesterol concentrations did not change significantly when the fat content of the diet was increased from 30% to 50% of total food energy. This was most likely due to the saturated fatty acid content being kept at 10% of energy in both diets. The test diet dramatically reduced 24-hour integrated glucose concentration and consequently the percent glycohemoglobin in people with type 2 diabetes. These positive results occur without a significant change in serum lipids, except for a significant decrease in triacylglycerol concentration.

Example 6

Results #2

The plasma α-amino nitrogen (AAN) concentration increased after meals, as expected. When the meals contained 15% protein (control diet), the AAN concentration increased with each meal but decreased to near basal levels between meals. However, when the diet contained 30% protein ($Diet_{20}$), only modest decreases were measured after breakfast and lunch. The AAN concentration did return to the fasting concentration overnight in all cases. The increase in AAN after the dinner meal in the control/pre is unexplained.

The net area response integrated over 24 hours using the fasting value as baseline were 2.6, 3.6, 4.8 and 15 mg·hr/dl in the control/pre, control/post, $Diet_{20}$/pre and $Diet_{20}$/post diets, respectively. Thus, the area response was ~3 fold greater after ingestion of the $Diet_{20}$, which contained twice as much protein ($p<0.05$). When the total area was calculated using zero as a baseline, the response to the $Diet_{20}$ again was significantly greater ($p<0.05$).

The fasting plasma urea nitrogen was 14-15 mg/dl before and after the control diet and before instituting the $Diet_{20}$. At the end of the 5-week period on the $Diet_{20}$, it had increased to 22 mg/dl. Thus, the $Diet_{20}$ at 30% protein resulted in a 57% increase in fasting plasma urea nitrogen. A gradual further small increase in urea nitrogen occurred throughout the day while ingesting the $Diet_{20}$, until the 17-hour time point, after which the concentration decreased to 21 mg/dl by the following morning. This late evening increase in concentration was nearly identical to that reported previously in subjects who ingested a 30% protein, 40% carbohydrate, 30% fat diet ($Diet_{40}$). The total urea nitrogen area response, using zero as baseline, was 45% greater ($p<0.05$) after ingestion of the $Diet_{20}$.

The calculated total amount of protein ingested during the 24-hour study period was compared with the total protein metabolized. After ingestion of the 15% protein meals (control), 106 g of protein were calculated to have been ingested and 92 g were calculated to have been metabolized (87%). After ingestion of the 30% protein meals ($Diet_{20}$), 212 g of protein were calculated to have been ingested and 142 g were calculated to have been metabolized (67%). This difference was statistically significant ($p<0.03$).

Serum growth hormone concentrations did not differ significantly between treatments. The serum IGF-1 concentration was similar before and after ingestion of the control diet and before ingestion of the $Diet_{20}$. However, it increased significantly from a mean of 115 to 161 ng/ml after 5 weeks on the $Diet_{20}$ ($p<0.01$).

Plasma renin activity was determined in 7 subjects. There was a mean increase when the subjects ingested the control diet. After institution of the $Diet_{20}$, plasma rennin activity decreased (Table 4). These differences were not statistically significantly different ($p=0.13$ and 0.20, respectively).

Mean 24-hour urinary aldosterone excretion was not different between diets. The mean urinary free cortisol was obtained in only 6 subjects. Mean urinary free cortisol increased by 44% consequent to the ingestion of the $Diet_{20}$, but this was not statistically significant ($p=0.17$).

Neither the serum TSH, free T4, nor the Total T3 were significantly affected by ingestion of the $Diet_{20}$, even though the $Diet_{20}$ contained much less carbohydrate than the control diet (Table 4).

Blood pressure remained unchanged. Serum homocysteine, folate and B12 also remained unchanged (Table 4). Urinary β-hydroxybutyrate excretion did not increase, nor did the urinary pH change when the subjects ingested the $Diet_{20}$ (Table 5). The creatinine clearance and microalbumin excretion also did not change. Sodium excretion was increased. The 24-hour urinary urea nitrogen increased when the subjects ingested the $Diet_{20}$. However, the mean increase was only ~60%, and not 2-fold as might be expected with a doubling of the protein content in the diet.

TABLE 4

Blood pressure, plasma/serum hormones, vitamins & metabolites

| | Control-Pre | Control-Post | $Diet_{20}$-Pre | $Diet_{20}$-Post |
|---|---|---|---|---|
| Blood Pressure (mm Hg) | 133/77 | 127/72 | 146/76 | 133/74 |
| Serum Creatinine (mg/dl) | 0.9 ± 0.1 | 0.9 ± 0.05 | 0.9 ± 0.05 | 1.0 ± 0.05* |
| Renin (ng/ml) | 0.64 ± 0.3 | 1.03 ± 0.3 | 0.69 ± 0.1 | 0.47 ± 0.1 |
| Serum Uric Acid (mg/dl) | 4.9 ± 0.2 | 5.5 ± 0.03 | 5.3 ± 0.3 | 5.8 ± 0.3 |
| TSH (μIU/ml) | 1.60 ± 0.22 | 1.49 ± 0.16 | 1.50 ± 0.13 | 1.39 ± 0.16 |
| Total $T_3$ (ng/dl) | 83.3 ± 8.5 | 79.6 ± 7.3 | 86.9 ± 7.9 | 81.9 ± 6.9 |
| Free $T_4$ (ng/dl) | 0.90 ± 0.04 | 0.85 ± 0.02 | 0.98 ± 0.05 | 1.04 ± 0.03 |
| Folate (ng/ml) | 16.5 ± 2.3 | 20.2 ± 1.2 | 18.0 ± 2.1 | 15.8 ± 2.2 |
| Homocysteine (μg/dl) | 8.1 ± 0.7 | 8.1 ± 0.8 | 8.9 ± 1.1 | 7.8 ± 2.1 |
| $B_{12}$ (pg/ml) | 524 ± 119 | 496 ± 99 | 557 ± 120 | 475 ± 108 |

Values are Mean ± SEM
*$p < 0.02$ compared to $Diet_{20}$-Pre

TABLE 5

Urine data

| | Control-Pre | Control-Post | $Diet_{20}$-Pre | $Diet_{20}$-Post |
|---|---|---|---|---|
| Volume (ml) | 4129 ± 707 | 3961 ± 691 | 4366 ± 502 | 4127 ± 558 |
| Glucose (g) | 22 ± 8 | 14 ± 4 | 17 ± 9 | 0.3 ± 0.3 |
| Potassium (mg) | 3315 ± 254 | 3471 ± 312 | 3471 ± 250 | 3081 ± 156 |
| Sodium (mg) | 5451 ± 276 | 5451 ± 713 | 4692 ± 253 | 6923 ± 759* |
| Urea (g) | 12.2 ± 0.9 | 13.3 ± 1.0 | 12.8 ± 0.9 | 20.6 ± 1.4* |
| Uric Acid (g) | 0.84 ± 0.12 | 0.72 ± 0.06 | 0.78 ± 0.11 | 0.90 ± 0.09† |

TABLE 5-continued

Urine data

|  | Control-Pre | Control-Post | Diet$_{20}$-Pre | Diet$_{20}$-Post |
|---|---|---|---|---|
| Micro albumin (mg) | N/A | 9.7 ± 1.7 | N/A | 8.3 ± 1.1 |
| β-OH butyrate (μM) | 187 ± 7 | 203 ± 10 | 196 ± 8 | 196 ± 8 |
| Calcium (g) | 220 ± 52 | 217 ± 62 | 221 ± 62 | 214 ± 64 |
| pH | 6.3 ± 0.1 | 6.2 ± 0.1 | 6.1 ± 0.1 | 6.2 ± 0.1 |
| Creatinine (g) | 1.8 ± 0.15 | 1.7 ± 0.13 | 1.8 ± 0.13 | 1.8 ± 0.15 |

TABLE 5-continued

Urine data

|  | Control-Pre | Control-Post | Diet$_{20}$-Pre | Diet$_{20}$-Post |
|---|---|---|---|---|
| Creatinine clearance (ml/min) | 143 ± 51 | 127 ± 45 | 144 ± 51 | 137 ± 48 |

Values are mean ± SEM
*p < 0.05 compared to Diet$_{20}$-Pre
†p = 0.06 compared to Diet$_{20}$-Pre B. Diet$_{30}$ Example 1

Participants

Eight men with mild, untreated type 2 diabetes were studied in a special diagnostic and treatment unit (SDTU), similar to a clinical research center. All participants met the National Diabetes Data Group criteria for the diagnosis of type 2 diabetes and were not being treated with oral hypoglycemic agents or insulin. Participant characteristics are given in Table 6. The Department of Veterans Affairs Medical Center and the University of Minnesota Committees on Human Subjects approved the study, and all participants gave written informed consent prior to enrollment in the study. Exclusion criteria included: hematological abnormalities, kidney disease, liver disease, macroalbuminuria (>300 mg/24 h), congestive heart failure, or untreated thyroid disease. before the study, participants were interviewed to determine their physical activity profile, any food aversions and to explain the study process and commitment in detail. Participants confirmed that they had been weight stable for at least 3 months. They were instructed to maintain their current activity level throughout the study. Two weeks before beginning the study, the participants completed a 3-day food questionnaire, with one of the days being a Saturday or a Sunday. This information was used to calculate the total food energy necessary to maintain body weight.

TABLE 6

Patient characteristics

| Patient | Age (yrs) | Height (cm) | Weight (kg) | BMI (kg/m$^2$) | tGHb (%) | Duration of diabetes (months) | Concomitant diseases | Medications |
|---|---|---|---|---|---|---|---|---|
| 1 | 50 | 175 | 97 | 32 | 10.0 | 42 | hypertension, hypercholesterolemia, multiple sclerosis, major depressive disorder, trigeminal neuralgia | bupropion, clonazepam, cyclobenzapine, gabapentin, glatiramer acetate, nifedipine, sertraline |
| 2 | 64 | 178 | 75 | 24 | 11.2 | 48 | hypertension, traumatic brain injury | none |
| 3 | 52 | 173 | 85 | 29 | 8.7 | 24 | none | aspirin |
| 4 | 67 | 183 | 92 | 28 | 11.0 | 180 | hypertension | none |
| 5 | 57 | 185 | 120 | 35 | 11.2 | 36 | dyslipidemia | none |
| 6 | 56 | 180 | 89 | 27 | 11.4 | 72 | seizure disorder, post-traumatic stress disorder | aspirin, phenytoin |
| 7 | 64 | 185 | 110 | 32 | 9.9 | 132 | hypertension, hypercholesterolemia | Atorvastatin, lisinopril |
| 8 | 62 | 175 | 82 | 27 | 12.7 | 66 | dyslipidemia, GERD | Simvastatin, ranitidine |
| Mean | 59 | 179 | 94 | 29 | 10.8 | 75 | — | — |
| Range | 50-67 | 173-185 | 75-120 | 24-35 | 8.7-12.7 | 24-180 | — | — |

Example 2

Diet

The study diet was designed to consist of 30% carbohydrate, 30% protein, and 40% fat. The saturated fatty acid content of the diet was approximately 10% of total food energy; thus, the majority of the fat was mono- and polyunsaturated. This diet is referred to as Diet$_{30}$. The diet composition of the Diet$_{30}$ is given in Table 7 and representative meals are shown in Table 8. Each patient was on the six-day rotation for a total of five weeks.

TABLE 7

| Composition of Diet$_{30}$ | |
|---|---|
| Protein (g) | 158 |
| Carbohydrates (g) | 155 |
| Fat (g) | 94 |
| Cholesterol (mg) | 450 |
| Dietary fiber (g) | 20 |
| Saturated fat | 12% |

TABLE 7-continued

Composition of Diet$_{30}$

| | |
|---|---|
| Monounsaturated fat | 16% |
| Polyunsaturated fat | 12% |
| Calories | 2109 |

TABLE 8

Sample Menu of Diet$_{30}$

Breakfast
Omelet:

4 ounces egg substitute
2 ounces cheddar cheese
2 slices bacon
1 green onion
¼ green pepper
2 slices pineapple
Lunch
Chef's salad:

1 hard cooked egg
2 ounces extra lean ham
2 ounces white turkey
⅓ cup celery
6 slices cucumber
1½ cups lettuce
1 ounce lite cheese
2 Tbsp Italian dressing
¼ cup water chestnuts
3 rye krisp wafers
1 tsp Fleishman's soft margarine
Supper 8 ounces broiled cod
1 cup asparagus
raw carrots and celery sticks
1 T Ranch dressing
½ cup brown rice
1 banana
Snack 2 ounces cottage cheese
2 halves peaches
2 ounces peanuts

Example 3

Experimental Plan

Participants were admitted to the SDTU on the evening prior to the study. The next day, standardized meals containing 55% carbohydrate, 30% fat, and 15% protein (control diet) were given for breakfast, lunch and dinner at 0800, 1200, and 1800. Participants were asked to remain in the SDTU during the study period with minimal activity.

On the second day in the SDTU, standardized meals again were given. In addition to the meals at 0800, 1200 and 1800, snacks were given at 1600 and 2100. Fasting blood was obtained at 0730, 0745, and 0800. Then samples were collected every 15 min for the first hour after meals, every 30 min for the next 2 h, and then hourly until the next meal. Blood was drawn at a total of 46 time points. After this 24-h data accumulation period, the participants were sent home with all of the necessary food for the next 2-3 days according to the Diet$_{30}$ menu plan.

Participants returned to the SDTU every 2-3 days to pick up food and meet with the study dietitian and study coordinator. At that time, the subjects provided a urine specimen for analysis of creatinine and urea to determine dietary compliance. They also were weighed and had blood pressure, total glycohemoglobin (tGHb), and blood glucose measured. If their body weight decreased or increased on two successive occasions, the total food energy of the meals was increased or decreased as appropriate to attempt to maintain stable weight throughout the study. In addition, participants were interviewed regarding dietary compliance during each visit. At the end of the 5-week period, the participants again were admitted to the SDTU and blood was drawn as described above. At this time, participants were given the meals (breakfast, lunch, dinner, and snacks) as appropriate for the day in the Diet$_{30}$ menu rotation.

Example 4

Biological Measurements

The plasma glucose concentration, HDL cholesterol, and total cholesterol were measured with the use of an automated method on an Ortho-Clinical Diagnostics Vitros 950 analyzer (Raritan, N.J.). LDL cholesterol was calculated with the Fridedwald Formulation. The β-hydroxybutyrate concentration was determined by colormetric assay (STANBIO, Boerne, Tex.). % tGHb was measured by boronate-affinity high-performance liquid chromatography (BioRad Variant; BioRad Labs, Hercules, Calif.). Serum immunoreactive insulin was measured using standard double-antibody radioimmunoassay kits from Incstar (Stillwater, Minn.). Glucagon and C-peptide were measured with radioimmunoassay kits from Linco Research (St. Louis, Mo.) and Diasorin (Stillwater, Minn.), respectively. Weight was determined in street clothes without shoes on a digital scale (Scalitronix, White Plains, N.Y.). Blood pressure was measured using a Dinemap instrument (Critikon/Mediq, Pennsauken, N.J.).

The plasma creatinine, plasma urea nitrogen, uric acid were measured with the use of an automated method on an Ortho-Clinical Diagnostics Vitros 950 analyzer (Raritan, N.J.). NEFAs were measured enzymatically using a kit manufactured by Wako Chemicals (Richmond, Va.).

The net 24-h incremental area responses were calculated using the overnight fasting value as baseline. Total 24-h area responses were calculated using zero as the baseline. Both area calculations were done using a computer program based on the trapezoid rule. Statistics were determined using Student's t test for paired variates, with the Statview 512+ program (Brain Power, Calabasas, Calif.) for the Macintosh computer (Apple Computer, Cupertino, Calif.). $P<0.05$ is the criterion for significance. Data are presented as the mean±SE. Prospective power calculation, with β equal to 90%, resulted in n=3.

Example 5

Results #1

The average body weight was 206±11.3 lb (94±5.1 kg) before the diet. At the end of the 5 weeks on the diet, the average weight was essentially unchanged 204±11.2 lb (93±5.1 kg).

Urine ketones were monitored twice weekly while participants were on the Diet$_{30}$. The majority of the samples were zero to trace using nitroprusside impregnated tablets (Bayer, Elkhart, Ind.); two single samples were positive for ketones.

The total area of the 24-h plasma β-hydroxybutyrate data was modestly higher after the Diet$_{30}$ but not significantly.

The mean fasting plasma glucose concentration decreased significantly from 227±18.6 mg/dl (12.6±1 mmol/L) to 130±14.3 mg/dl (7.2±0.79 mmol/L; P=0.001) after 5 weeks on the die). The mean 24-h integrated net glucose area response decreased from 1269±269 mg·hr/dl (70.5±14.9 μmol·hr/L) to 449±129 mg·hr/dl (24.9±7.2 μmol·hr/L) (P=0.001). The total area response decreased from 6717±501 mg·hr/dl (373±27.8 μmol·hr/L) to 3724±348 mg·hr/dl (207±19.3 μmol·hr/L; P=0.0001).

The mean fasting serum insulin concentration was unchanged (8.4±1.1 μU/ml (50.4±6.6 pmol/L) and 9.0±1.0 μU/ml (54±6 pmol/L)) before and after 5 weeks on the diet, respectively. The mean 24-h integrated net insulin area response and the total integrated insulin area response also remained essentially unchanged after 5 weeks on the diet.

The mean fasting serum C-peptide concentration also was unchanged after 5 weeks on the diet (0.6±0.1 ng/ml to 0.8±0.2 ng/ml, P=0.3). The 24-h time course response was similar to the insulin response. The net C-peptide area response decreased from 11.4±2.4 ng·hr/ml to 10.6±1.4 ng~hr/ml after 5 weeks on the $Diet_{30}$. This was not statistically significant (P>0.05). The 24-h total area did not change before or after the diet, 25±2.9 ng·hr/ml to 25.8±2.54 ng·hr/ml respectively.

The mean % tGHB decreased from 10.8±0.4% to 9.1±0.5%, before and after the diet respectively (P<0.0001). In addition, at the end of the study, it was still decreasing in an essentially linear fashion.

The mean fasting plasma glucagon concentrations were similar before and after the diet; 76±3.1 pg/ml and 77±11.1 pg/ml, respectively. Both the 24-1 integrated net response and the 24-h total area response increased after 5 weeks on the diet. These were not statistically significant (P=0.33 and P=0.32, respectively).

The mean fasting plasma triacylglycerol concentration significantly decreased from 190±24.5 mg/dl to 113±9.4 mg/dl after 5 weeks on the diet (P=0.007); however the decrease seen with the 24-h net area was not statistically significantly. The 24-h total area response significantly decreased from 5695±806 mg·hr/ml to 3586±326 mg·hr/ml (P=0.008). The total cholesterol concentration significantly decreased from 189 mg/dl to 152 mg/dl after 5 weeks on the diet (P=0.004). The plasma LDL and HDL concentration decreased from 113 to 95 and from 37 to 34, respectively, which was not significant.

Example 6

Results #2

The mean fasting NEFA concentrations decreased from 691±74.6 μEq/L to 622±54.8 μEq/L. This was not statistically significant (P>0.05). The mean 24-h integrated net NEFA area response was increased after 5 weeks on the $Diet_{30}$, however this was not significant (P>0.05). Differences in the 24-h total areas were also not statistically significant.

The mean fasting alpha amino acid nitrogen concentration was 4.01±0.1 mg/dl before the diet and remained unchanged after 5 weeks on the diet. The 24-h integrated net and 24-h total area responses were significantly increased after 5-weeks on the $Diet_{30}$.

The mean fasting plasma creatinine level remained unchanged, 0.9 mg/dl and 0.9 mg/dl, before and after the diet respectively. However, the mean 24-h integrated net creatinine response increased from 0.3±0.3 mg·hr/dl to 1.7±0.5 mg·hr/dl (P=0.768). This difference was also present when correcting for the baseline with the 24-h total area response.

The mean fasting uric acid concentration increased from 4.7±0.4 mg/dl to 5.5±0.4 mg/dl (P=0.002) and remained elevated throughout the 24-h study period. The 24-h net area decreased modestly after 5 weeks on the diet (P=0.9). However, the 24-h integrated total area significantly increased from 106±9.6 mg·hr/dl to 124±8.2 mg·hr/dl (P=0.0013).

The mean fasting plasma urea nitrogen concentration increased from 15±1 mg/dl to 19±1.8 mg/dl after 5 weeks on the diet (P<0.05). The 24-h net area response increased from −4±7.1 mg·hr/ml to 28±11.7 mg·hr/ml; however this was not significant (P=0.09). The 24-h integrated total area increased from 346±22 mg/dl to 479±42 mg/dl (P=0.0038).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing glycohemoglobin and fasting glucose levels in an individual, comprising:
providing an article of manufacture, wherein the article of manufacture comprises food items for a single day, wherein the food items have a nutritional composition that consists essentially of 30% protein, 40% fats, and 30% carbohydrates, and
having the individual consume the food items each day for a period of five weeks to significantly reduce the levels of glycohemoglobin and fasting glucose in the individual.

2. The method of claim 1, wherein ingestion of the food items does not result in ketosis in the individual.

3. The method of claim 1, wherein ingestion of the food items results in maintenance of the individual's weight.

4. The method of claim 1, wherein ingestion of the food items does not result in the individual losing weight.

* * * * *